United States Patent
Sawyer et al.

(10) Patent No.: US 8,734,879 B2
(45) Date of Patent: *May 27, 2014

(54) METHODS OF PRESERVATION

(71) Applicant: Nevada Naturals Inc., Albuquerque, NM (US)

(72) Inventors: Anthony J. Sawyer, Albuquerque, NM (US); Richard F. Stockel, Bridgewater, NJ (US)

(73) Assignee: Nevada Naturals Inc., Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/930,929

(22) Filed: Jun. 28, 2013

(65) Prior Publication Data

US 2013/0289111 A1 Oct. 31, 2013

Related U.S. Application Data

(60) Division of application No. 13/065,972, filed on Apr. 4, 2011, now abandoned, which is a continuation of application No. 12/455,197, filed on May 28, 2009, now Pat. No. 8,193,244.

(60) Provisional application No. 61/341,702, filed on Apr. 3, 2010.

(51) Int. Cl.
*A21D 4/00* (2006.01)

(52) U.S. Cl.
USPC .......... 426/335; 426/392; 426/410; 426/532; 424/401; 424/405

(58) Field of Classification Search
USPC ...................................... 426/335
See application file for complete search history.

(56) References Cited

U.S. PATENT DOCUMENTS 8,193,244 B1  6/2012  Stockel et al.
2012/0087968 A1  4/2012  Ebner

OTHER PUBLICATIONS

Appendini: Review of antimicrobial food packaging; Innovative Food Science & Emerging Technologies 3; 2002; p. 113-126.*
No new references cited.*
Sangster, James. "Octanol-Water Partition Coefficients of Simple Organic Compounds," Sangster Research Laboratories, J. Phys. Chem. Ref. Data, vol. 18, No. 3 (1989), pp. 1111-1227.
Whitworth, Joe. "Migration levels of antimicrobial packaging material found to be safe." Food Production Daily.com. Mar. 19, 2013. Web. Dec. 9, 2013. <http://www.foodproductiondaily.com/Safety-Regulation/Migration-levels-of-antimicrobial-packaging-material-found-to-be-safe>.

* cited by examiner

*Primary Examiner* — Patricia George
(74) *Attorney, Agent, or Firm* — Posz Law Group, PLC

(57) ABSTRACT

This invention discloses a method of preservation of a food product comprising the step of adding 1) a first component comprising between 10 ppm and 1% of a biocidal salt of $N^{\alpha}$-(C1-C22) alkanoyl di-basic amino acid alkyl (C1-C22) ester cationic biocidal molecule with an anionic counterion, and 2) a second component comprising from 10 ppm to 1% by weight an acyl monoglyceride, directly to a food product. The preferred cationic biocidal molecule comprises $N^{\alpha}$-lauroyl-L-arginine ethyl ester ("LAE"). The invention also discloses the method of preservation of a food product using salts of a $N^{\alpha}$-(C1-C22) alkanoyl di-basic amino acid alkyl (C1-C22) ester cationic biocidal molecule and an anionic counterion with or without a monoglyceride of a fatty acid, whereby the packaging film is compounded with the salts and the optional monoglyceride of a fatty acid.

13 Claims, No Drawings

METHODS OF PRESERVATION

REFERENCE TO RELATED APPLICATIONS

This application is a divisional of U.S. Ser. No. 13/065,972, filed Apr. 4, 2011, which claims the benefit of application Ser. No. 12/455,197, filed May 28, 2009. This application also claims the benefit of provisional application Ser. No. 61/341,702, filed Apr. 3, 2010. The disclosures of all of the foregoing applications are incorporated by reference herein in their entirety.

FIELD OF THE INVENTION

The invention relates to a method of preservation using biocidal compositions that are environmentally safe that can have antimicrobial, antibacterial, antiviral, and antifungal properties. The method of preservation uses salts of a cation of a $N^\alpha$-(C1-C22) alkanoyl di-basic amino acid alkyl (C1-C22) ester biocidal molecule and an anion of a monomeric molecule with or without a monoglyceride of a fatty acid.

BACKGROUND OF THE INVENTION

The use of environmentally beneficial compositions, especially those that are referred to as "green", is important in choosing biocidal materials that can be used as preservatives. The use of natural or naturally-derived materials is also very much of interest in ingested compositions. It is also important that both green and naturally-derived materials be utilized in a composition that will provide antimicrobial, antibacterial, antifungal, and antiviral properties as well as preservative capability. If all of the components of a biocidal composition are GRAS (Generally Regarded as Safe) and are approved for food use, the resulting composition could also be ingested with little or no side effects.

Although $N^\alpha$-(C1-C22) alkanoyl di-basic amino acid alkyl (C1-C22) ester salts have been known since the 1960's, one of the first patents to recommend these amino acids, specifically for food applications was U.S. Pat. No. 3,825,560 (issued Jul. 23, 1979). A number of derivatives are disclosed including $N^\alpha$-cocoyl-L-arginine ethyl ester pyrrolidone carboxylate and $N^\alpha$-lauroyl-L-arginine methyl ester hydrochloride. Since this publication there have been several more patents issued or published disclosing specifically $N^\alpha$-lauroyl-L-arginine ethyl ester hydrochloride salt ("LAE"). These include U.S. Pat. No. 5,780,658 that discloses a process to prepare LAE, as well as disclosing its use for food applications. U.S. Pat. No. 7,074,447 B2 discloses an antimicrobial composition comprising LAE with potassium sorbate. U.S. Pat. No. 7,087,769 is another process patent suggesting its use for food. Two patent publications, U.S. 2004/0166082 and U.S. 2004/0175350, disclosure di basic amino acid alkyl ester salts useful for cosmetic applications. U.S. 2004/0254232 covers oral care while U.S. 2004/0265443 covers food. U.S. 2005/0175747 discloses complexes formed between LAE and various anionic hydrocolloids. All of the above references are incorporated into the body of our present invention.

One of the purposes of this invention is to utilize a synergistic mixture of $N^\alpha$-long chain alkanoyl di basic amino acid alkyl ester salt type biocide that will increase the preservative performance compared to the sole use of $N^\alpha$-long chain alkanoyl di basic amino acid alkyl ester salts. By combining glycerol esters of fatty acids, with chain lengths of from C6 to C14 with $N^\alpha$-long chain alkanoyl di basic amino acid alkyl ester salts, a significant broadening of cidal activity is achieved. Furthermore, this synergistic mixture allows the use of much lower levels of either biocide while maintaining biocidal efficacy and thereby reduces cost.

The literature is replete with numerous references concerning glycerol monofatty acid esters having antiviral and antibacterial activity. The most active monoglycerides consist of those esters formed from saturated fatty acids having from 6 to 14 carbon atoms. U.S. Pat. No. 4,997,851 teaches the use of saturated fatty acids and glycerol monofatty acid esters as effective antiviral agents against the HIV and HSV-1 viruses. They were also active against a variety of gram positive and gram-negative bacteria.

U.S. Pat. No. 5,434,182 discloses the spermicidal, antimicrobial and cytocidal activity of glycerol monofatty acid esters. It discloses the combination of fatty acyl glycerides, a chelating acid, and a surfactant, which confer excellent antimicrobial activity for preserving processed meats and for disinfecting poultry carcasses. When only one of these three agents was used, the anti-microbial performance was considerably reduced. U.S. Pat. No. 6,414,023 B1 discloses the use of fatty acid monoglycerides in conjunction with 2,4-dichlorobenzyl alcohol.

John J. Kabara in U.S. Pat. No. 6,638,978 B1 lists a preservative formulation for food and cosmetics consisting of monolaurin (ML), caprylic and capric acid mixture, and propylene glycol in an aqueous base. U.S. 2005/0084471 A1 teaches the preparation of a preservative for meat, fruits, and vegetables and for the disinfection of inanimate surfaces. The actives include a propylene glycol C7-C14 fatty acid ester as the major component, a surfactant, and an enhancer. Enhancers include phenolic antioxidants and/or a paraben ester. Lastly, U.S. Patent 2006/0030512 A1 describes a long lasting anti-microbial film comprising a glycerol monoester, an amphoteric surfactant, a chelating agent and a solvent like propyl alcohol plus other incipients. All of the above references are incorporated into the body of our present invention.

OBJECTS OF THE INVENTION

It is an object of the invention to provide methods of preservation using compositions that are environmentally safe that can have antimicrobial, antibacterial, antiviral, and antifungal properties.

It is an additional object of the invention to provide methods for the preservation of food products that utilize GRAS materials such that the materials will be lethal to the microorganisms found in such food products.

It is a further object of the invention to provide methods for the preservation of food products involving the use of GRAS materials that will not only be safe and efficacious, but also have a long-lasting lethality to microorganisms found in such food products by incorporating the compositions of this invention into packaging or related materials that would come in contact with food. It is an unanticipated discovery of this invention that the more water soluble salts of $N\alpha$-(C1-C22) alkanoyl di-basic amino acid alkyl (C1-C22) ester cationic biocidal compounds of this invention have shown effective preservation for food when incorporated into plastic packaging film (Table 3). While U.S. 2010/0173993 and U.S. 2010/0056628 teach that salts of this invention with limited solubility are effective for preservation of packaged food products when incorporated into plastic packaging, it was found through experimentation that the more water soluble salts of $N^\alpha$-(C1-C22) alkanoyl di-basic amino acid alkyl (C1-C22) ester cationic biocidal compounds will also provide for preservation of packaged food products.

DETAILED DESCRIPTION OF THE INVENTION

The invention pertains to a method of preservation of food products using environmentally safe biocidal compositions that have antimicrobial, antibacterial, antifungal and antiviral properties. Such compositions can be considered to be green and natural or naturally derived and are particularly useful for the preservation of foods.

This invention covers the use of $N^\alpha$-(C1-C22) alkanoyl di-basic amino acid alkyl (C1-C22) ester cationic biocidal compounds. A preferred embodiment of the invention uses these compounds with a fatty acid (C8-C14) glycerol ester. Thus one component of a synergistic system of this invention is an $N^\alpha$-long chain alkanoyl di basic amino acid alkyl ester salt and the other is glyceryl monoalkanoate ester (acyl monoglyceride) having from 6 to 14 carbon atoms. $N^\alpha$-long chain alkanoyl di basic amino acid alkyl ester salts are naturally derived from renewable source. Glyceryl monoalkanoates have a long history of safety and a low toxicity profile and are found naturally. They can also be manufactured synthetically from natural ingredients.

Specifically, the $N^\alpha$-(C1-C22) alkanoyl di-basic amino acid alkyl (C1-C22) ester cationic biocidal molecule salts of interest are the salts of $N^\alpha$-(C1-C22) alkanoyl di-basic amino acid alkyl (C1-C22) ester of L-arginine, L-histidine, L-tryptophan and L-lysine with an anionic counterion. Any anionic counterion may be used for this purpose. Suitable anionics counterions include but are not limited to halides, e.g. chloride and bromide, hydrogen sulfate, acetate, glycerophosphate, gluconate, phosphonates, phosphinates, phenolates, and polyphenolates, and anions of carboxylic acids from C1 to C3, hydroxy carboxylics from C3-C6, or mono- and dihydrogen phosphates, mono- and dihydrogen phosphonates, and mono- and dihydrogen phosphinates.

Particularly preferred examples of suitable $N^\alpha$-(C1-C22) alkanoyl di-basic amino acid alkyl (C1-C22) ester cationic biocidal molecule salts include but are not limited to the salts of $N^\alpha$-lauroyl and $N^\alpha$-cocoyl ethyl arginate.

A particularly preferred example of a fatty acid (C8-C14) glycerol ester of an acyl monoglyceride is monoglyceryl laurate.

When added directly to food or food products, the $N^\alpha$-(C1-C22) alkanoyl di-basic amino acid alkyl (C1-C22) ester cationic biocidal molecule salts should be used at concentrations between 10 ppm and 1% by weight and the acyl monoglycerides are used at concentrations between 10 ppm and 1% by weight.

In addition to the outstanding antimicrobial properties of certain $N^\alpha$-(C1-C22) alkanoyl di-basic amino acid alkyl (C1-C22) ester salts, these salts are especially safe for humans and the environment. These salts completely biodegrade into endogenous natural products resulting in very low overall toxicity for both humans and the environment.

The use of combinations of $N^\alpha$-(C1-C22) alkanoyl di-basic amino acid alkyl (C1-C22) ester salts with glycerol monofatty acid esters have several advantages over other antimicrobials. One concern of using biocidally active cationic compounds such as $N^\alpha$-(C1-C22) alkanoyl di-basic amino acid alkyl (C1-C22) ester salts as preservatives is the possible loss of cationic entities over time due to coupling with anionic species present or released by the food being preserved. The use of glycerol monofatty acid esters (acyl monoglycerides) as co-biocides with these cationic agents ensures that some preservative will remain active after loss of the cationic agent.

By microbial and organoleptic testing it has been found that a synergistic combination of $N^\alpha$-(C1-C22) alkanoyl di-basic amino acid alkyl (C1-C22) ester salts with glycerol monofatty acid esters can result in several improvements as listed below:

Broadening of antimicrobial activity
Lengthening of time that the solutions retain antimicrobial activity
Improved cost-effectiveness
The production of organolepticly satisfying products
Ease of application Experimentally, it has been found that the level of the $N^\alpha$-(C1-C22) alkanoyl di-basic amino acid alkyl (C1-C22) ester salts of this invention for adequate antimicrobial activity when added directly to food or food products should be from about 10 ppm to about 500 ppm, preferably from about 75 ppm to about 300 ppm, and most preferably from about 100 ppm to about 250 ppm. By including glycerol monofatty esters, the $N^\alpha$-(C1-C22) alkanoyl di-basic amino acid alkyl (C1-C22) ester salt level can be reduced by about 10 ppm to about 150 ppm rather than the higher levels. Some organisms such as viruses, yeast, fungi, or mold might require the use of higher levels of $N^\alpha$-(C1-C22) alkanoyl di-basic amino acid alkyl (C1-C22) ester salts, possibly up to 1.0% by weight. Also under some conditions to function as a preservative the usage level of $N^\alpha$-(C1-C22) alkanoyl di-basic amino acid alkyl (C1-C22) ester salts may have to be as high as 1% by weight based on the weight of the packaging material, depending on what other ingredients are present in a particular formulation. When using the method of preservation of this invention, by incorporating the biocides of this invention into bulk plastic food packaging, much higher levels of the biocides, possibly up to 50,000 ppm might be required, based on the weight of the packaging material.

Compositions of this invention can be effective in the pH range between about 2 and 10.0. However, at pHs of about 3.5 and lower and at 8.5 and higher the $N^\alpha$-long chain (C8 to C16) alkanoyl di basic amino acid alkyl (C1 to C4) ester salts tend to hydrolyze. Therefore a more ideal pH range for their use is between pH 4.0 and 8.0 even more preferable between pH 4.0 and 7.0.

Other ingredients can be used to help the effectiveness of the preservative compounds used in the invention. These include, for example, solvents or surfactants to promote solubility or dispersion within the products being preserved. In addition, other antimicrobial agents might provide synergistic activity with preservatives of the invention allowing lower concentrations to be used. When the biocidal compositions utilized in the method of use of this invention are applied for direct contact to food, they can be dispensed as solutions, dispersions, solids, or aerosols.

Example 1

Synergistic Preservative Action of $N^\alpha$-Lauroyl Arginine Ethyl Ester (LAE)

The results are set forth below in Table 1.

TABLE 1

The synergistic preservative action of $N^\alpha$-lauroyl arginine ethyl ester (LAE) with glycerol monolaurate

| Monolaurin ppm | LAE ppm | | | | | | | | | |
|---|---|---|---|---|---|---|---|---|---|---|
| | 120 | 100 | 80 | 60 | 40 | 30 | 20 | 15 | 10 | 7.5 |
| 0 | 0 | 0 | 0 | 0 | 0 | 0 | 0 | G | G | G | G |
| 10 | 0 | 0 | 0 | 0 | 0 | 0 | 0 | 0 | G | G | G |
| 20 | 0 | 0 | 0 | 0 | 0 | 0 | 0 | 0 | 0 | G | G |
| 30 | 0 | 0 | 0 | 0 | 0 | 0 | 0 | 0 | 0 | G | G |
| 40 | 0 | 0 | 0 | 0 | 0 | 0 | 0 | 0 | 0 | 0 | G |

TABLE 1-continued

The synergistic preservative action of N$^\alpha$-lauroyl arginine ethyl ester (LAE) with glycerol monolaurate

| Monolaurin ppm | LAE ppm | | | | | | | | | |
|---|---|---|---|---|---|---|---|---|---|---|
| | 120 | 100 | 80 | 60 | 40 | 30 | 20 | 15 | 10 | 7.5 |
| 50 | 0 | 0 | 0 | 0 | 0 | 0 | 0 | 0 | G | G |
| 60 | 0 | 0 | 0 | 0 | 0 | 0 | 0 | 0 | G | G |
| 70 | 0 | 0 | 0 | 0 | 0 | 0 | 0 | 0 | G | G |
| 80 | 0 | 0 | 0 | 0 | 0 | PT | PT | G | G | G |
| 90 | 0 | 0 | 0 | 0 | PT | PT | PT | G | G | G |
| 100 | 0 | 0 | 0 | 0 | PT | PT | PT | G | G | G |

The results in Table 1 clearly indicate synergy between LAE and glycerol monolaurate ("monolaurin") as a combination preservative. Thus used in the amounts of 10 ppm LAE with 40 ppm Monolaurin, complete growth inhibition of candida albicans is obtained whereas when used alone, 30 ppm of LAE or much more than 100 ppm monolaurin would be required to achieve growth inhibition.

Example 2

Time Kill Test

The results are set forth below in Table 2.

TABLE 2

Time Kill Test at 90 seconds with a LAE concentration at 500 ppm and ML concentration at 45 ppm.

| Organism | Log Reduction |
|---|---|
| *Klebsiella pneumoniae* | >2.0 |
| *Pseudomonas aeruginosa* | >2.0 |

The method of preservation of this invention can be used by incorporating the biocidal salts in equipment for handling blood products such as blood sera, test tubes, vacutainer tubes, and other blood handling items; plasma bags; disposable gloves; condoms; band-aids, or bandages; and feminine hygiene products including but not limited to sanitary napkins and tampons.

The methods of preservation of this invention comprise utilizing a salt of a cation of a N$^\alpha$-(C1-C22) alkanoyl di-basic amino acid alkyl (C1-C22) ester cationic biocidal molecule and an anion consisting of acetate, sulphate, chloride, or bromide.

Preferably, the di-basic amino acid of the first component is selected from the group consisting of arginine, lysine, histidine and tryptophan. The most preferred cationic biocidal molecule is N$^\alpha$-lauroyl-L-arginine ethyl ester, hereinafter frequently referred to as "LAE".

For the applications of this invention for direct food contact, it is required that the salts utilized for the methods of preservation of the invention include the addition of a saturated C6-C14 fatty acid monoglyceride such as glycerol monolaurate. The monolaurate is utilized in an amount of about 10 ppm to about 1% by weight.

The salts of the invention may be prepared by any suitable reaction. For example they can be produced from a metathesis reaction between an acid salt of the first component and an alkali or alkaline earth metal salt of the second component. Alternatively, the salts of the invention may be prepared by an acid-base reaction between the first component present in the form of its free base and the second component present in the form of an undissociated molecule having a transferable proton. Other methods of preparation are potentially available by anyone skilled in the art of organic synthesis.

Applications

The applications for the methods of preservation utilizing biocidal compositions of the invention are suitable for a wide range of applications. It should be understood that this list is presented for illustrative purposes only and does not represent any limitation as to possible applications. It should be further understood that it is within the purview of this invention that the products described below may be combined with conventional, antibacterial agents, and/or antifungal agents.

Applications of the method of preservation of the invention by incorporating the biocides of this invention into certain articles are as follows:

(1) impregnated personal care materials: patches and strips for skin treatment; skin surface implants; diapers;

(2) impregnated dental care materials: dental floss; toothbrush bristles; orthodontic appliance; orthodontic appliance adhesive; denture appliance; endo-dontic articles.

(3) Impregnated plastics and miscellaneous products, including: medical items, e.g., thermometers, catheters, surgical sutures, blood lines, implants, bandages, surgical dressings, surgical apparel, respirators, etc.; food packaging; fluid-dispensing tubing; drug and cosmetic packaging; eating utensils; shower curtains; bath mats; sponges; mops; toilet seats, rubber gloves; contact lenses; hearing aids; shelving paper; carpet pads; pool covers; animal bedding and cat litter; computer covers and computer keys; doorknobs; tampons and sanitary napkins; adult novelties; sexual aids; sex toys; condoms; pregnancy barriers; dental chairs; dryer sheets; dishcloths; paints and coatings; filters; foams; hair brushes; combs; intravenous and plasma bags; disposable gloves; blood sample tubes to inactivate HIV, HCMV, and other viruses; condoms, band-aids, and bandages;

(5) Impregnated fibers and fabrics including natural and synthetic fibers and fabrics manufactured from such fibers; wipes, cloths; surgical gauze; crib covers; bassinet covers; bed linens; towels and wash cloths; tents; draw sheets; cubicle curtains; shower curtains; wall coverings; wood and wood products; hospital clothing such as examination robes, physicians' coats, nurses uniforms, etc.; apparel; paper, non-woven fabric, knitted fabric, woven fabric, brick, stone, plastic, polymer, latex, metal, tile, walls, floors, gurneys, tables, or trays; shoes.

Foods and food products that can utilize the method of preservation of this invention by direct contact or by incorporating the components of this invention into packaging materials are: food-stuffs; animal feed-stuffs; grains; breads; bakery products; confectionary; potato products; pasta products; salads; soups; seasonings; condiments; syrups; jams, jellies and marmalades; dairy products; egg-based products; meats and meat-based products; poultry and poultry-based products; fish and fish-based products; crustaceans and crustacean-based products; fresh and dried fruit products; vegetables and vegetable products; greens; salads; sauces; beverages, e.g., wines, tea extracts, beers, juices.

In respect to direct contact of food products, the biocidal compositions used in the method of preservation of the invention will typically be applied to the food product in the form of an aqueous emulsion or microemulsion. Experimentally, it has been found that the level of the N$^\alpha$-(C1-C22) alkanoyl di-basic amino acid alkyl (C1-C22) ester salts for adequate antimicrobial activity should be from about 10 to about 500 ppm, preferably from about 75 to about 300 ppm, and most preferably from about 100 ppm to about 250 ppm. The composition may be applied to the food product by conventional techniques, e.g., spraying, immersion, dipping or injection.

Instead of, or in addition to, contacting the food product directly with the composition, the composition may be incorporated in a suitable packaging material by techniques such as dissolution in thermoplastic resins, melt spun or melt blown into the packaging material, etc. The packaging material may be any GRAS material, e.g. a thermoplastic material such as a polyolefin and copolymers thereof, polyesters, polyvinyl chloride, polyacrylate, polyamide, etc., that is suitable for packaging food products. Suitable packaging materials include metallocene-type polyethylene, polylactic acid, bioplastics based on starch, cellulose and polyester, polyethylene, polypropylene, poly(ethylene-vinyl acetate), polystyrene, polyvinylidene chloride, ionomers, polyethylene terphthalates, polyvinyl acetate, polycarbonate, polyamides, polyvinyl alcohols, cellulose and modified cellulose including chitosan, polyethylene copolymers, polypropylene copolymers, poly(ethylene-vinyl acetate) copolymers, polystyrene copolymers, polyvinyl chloride copolymers, polyvinylidene chloride copolymers, ionomers, polyethylene terphthalate copolymers, polyvinyl acetate copolymers, polycarbonate copolymers, polyamides copolymers, polyvinyl alcohol copolymers, and cellulose and modified cellulose copolymers including chitosan.

The method of preservation for food products of this invention can include impregnating the packaging material with or incorporating into the packaging material the biocidal compositions specified in the invention which would then be placed in contact with the food product. This technique would result in a wrapped perishable food with a greatly increased amount of preservative that finds its way into the food product or onto the food surface. Experimentally, it has been found that the level of the $N^\alpha$-(C1-C22) alkanoyl di-basic amino acid alkyl (C1-C22) ester salts incorporated into a plastic packaging film for adequate antimicrobial activity for preservation of food products should be from about 500 ppm to about 5% by weight based on the packaging material, preferably from about 250 ppm to about 2% by weight, and most preferably from about 100 ppm to about 1% by weight, depending on the particular plastic packaging film. For many applications for incorporating the biocidal compositions specified in this invention into a food product packaging material or impregnating the biocidal compositions specified in this invention into a food product packaging material, it is desirable that the salts utilized for the methods of preservation of the invention include the addition of a saturated C6-C14 fatty acid monoglyceride such as glycerol monolaurate. If present, the monolaurate is utilized in an amount of about 10 ppm to about 1% by weight, based on the weight of the packaging material.

Example 3

Antimicrobial Activity of Compounded Films

Two beef loins from a slaughterhouse were tested in a heat-sealed package simulating food packaging. The linear low density polyethylene film was compounded with 1% by weight LAE-HCl biocidal salt based on the weight of the film. The results are reported in Table 3 below. The log colony forming units ("CFU") reduction values for bacteria that are part of the background flora of raw meat for both samples are 42 days indicate that there is a release of the salt of the invention from the polyethylene film to the surrounding beef surfaces.

TABLE 3

Antimicrobial Activity of Compounded Films

| Sample ID | Log CFU/g | | | | | Day 42 Log Reduction Vs. Control | Day 42 CFU/g | Day 42 % Reduction Vs. Control |
|---|---|---|---|---|---|---|---|---|
| Days | 7 | 14 | 21 | 28 | 42 | | | |
| lo in 1 film (control) | 2.82 | 4.68 | 5.63 | 7.06 | 7.24 | 0 | 17,278,687 | 0 |
| lo in 2 film 1% LAE HCl | 2.31 | 3.68 | 3.97 | 5.32 | 5.57 | 167 | 371,282 | 97.9 |

The invention claimed is:

1. A method of preserving food with a food packaging preservative material comprising:
   providing a packaging material, comprising:
   a biocidal salt, comprising a salt of N alpha-lauroyl-L-arginine ethyl ester (LAE) comprising anionic counterions; and
   an acyl monoglyceride, comprising glycerol monolaurate;
   incorporating the packaging material into a polymeric material by a technique selected from the group comprising: dissolution in thermoplastic resins, melt spun or melt blown into the polymeric material to form a food packaging preservative material;
   packaging said food product with the food packaging preservative material by contacting the food product with the food packaging preservative material.

2. The method of claim 1, wherein said contacting increases the amount of biocidal salt on said food product, and reduces the amount of the biocidal salt of the food packaging preservative material, in an amount of about 10 ppm to 1% by weight based on the weight of the food packaging preservative material.

3. The method of claim 1 wherein said anionic counterion is selected from group consisting of a halide, sulfate, C1-C3 carboxylate, C1-C6 hydroxycarboxylate, glycerophosphate, C2-C4 di- or tri-carboxylate, mono, and di phosphate, mono- and di-phosphonate, mono- and d-phosphinate, phenolate and polyphenolate.

4. A food packaging preservative material comprising:
   a biocidal salt, comprising a salt of N alpha-lauroyl-L-arginine ethyl ester (LAE) comprising anionic counterions; and
   an acyl monoglyceride, comprising glycerol monolaurate.

5. The food packaging preservative material of claim 4, wherein said anionic counterion is selected from the group consisting of a halide, hydrogen sulfate, C1-C3 carboxylate, C1-C6 hydroxycarboxylate, glycerophosphate, C2-C4 di- or tri-carboxylate, mono, and di phosphate, mono- and di-phosphonate, mono- and d-phosphinate, phenolate and polyphenolate.

6. The food packaging preservative material of claim 5, wherein said halide is selected from the group consisting of chloride and bromide.

7. The food packaging preservative material of claim 5, wherein said C1-C3 carboxylate is selected from the group consisting of formate, acetate, and propionate.

8. The food packaging preservative material of claim 5, wherein said C1-C6 hydroxycarboxylate is selected from the group consisting of lactate, malate, tartrate, citrate, and gluconate.

9. The food packaging preservative material of claim 5, wherein said C2-C4 di or tri-carboxylate is selected from the group consisting of succinate and malonate.

10. The food packaging preservative material of claim 4, wherein said polymeric material is in the form of a packaging film.

11. The food packaging preservative material of claim 4, wherein the amount of the biocidal salt is reduced to 10 ppm to 1% by weight based on the weight of the food packaging preservative material.

12. The food packaging preservation material of claim 11, wherein said acyl monoglyceride is in an amount of from 10 ppm to 1% by weight of said packaging material.

13. The food packaging preservation material of claim 4, wherein said polymeric material is selected from the group consisting of polyolefins and polyolefin copolymers, polyester, polyacrylate, and polyamide, metallocene-type polyethylene, polylactic acid, bioplastics based on starch, cellulose and polyester, polyethylene, polypropylene, poly(ethylene-vinyl acetate), polystyrene, polyvinyl chloride, polyvinylidene chloride, ionomers, polyethylene terphthalates, polyvinyl acetate, polycarbonate, polyamides, polyvinyl alcohols, cellulose and modified cellulose including chitosan, polyethylene copolymers, polypropylene copolymers, poly(ethylene-vinylacetate) copolymers, polystyrene copolymers, polyvinyl chloride copolymers, polyvinylidene chloride copolymers, polyethylene terphthalate copolymers, polyvinyl acetate copolymers, polycarbonate copolymers, polyamides copolymers, polyvinyl alcohol copolymers, and cellulose and modified cellulose copolymers including chitosan.

* * * * *